(12) United States Patent
Masini et al.

(10) Patent No.: US 7,920,162 B2
(45) Date of Patent: Apr. 5, 2011

(54) DISPLAY METHOD AND SYSTEM FOR SURGICAL PROCEDURES

(75) Inventors: Michael A. Masini, Ann Arbor, MI (US); Amir Sarvestani, Freiburg (DE)

(73) Assignee: Stryker Leibinger GmbH & Co. KG, Freiburg (DE)

( * ) Notice: Subject to any disclaimer, the term of this patent is extended or adjusted under 35 U.S.C. 154(b) by 1359 days.

(21) Appl. No.: 11/435,246

(22) Filed: May 16, 2006

(65) Prior Publication Data

US 2007/0282195 A1    Dec. 6, 2007

(51) Int. Cl.
*H04N 7/18* (2006.01)
*H04N 5/253* (2006.01)
(52) U.S. Cl. .......................................... 348/77; 600/406
(58) Field of Classification Search ..................... 348/77; 600/406
See application file for complete search history.

(56) References Cited

U.S. PATENT DOCUMENTS

| 6,459,926 | B1 * | 10/2002 | Nowlin et al. ................ 600/429 |
| 6,643,124 | B1 * | 11/2003 | Wilk ......................... 361/679.04 |
| 6,659,939 | B2 * | 12/2003 | Moll et al. .................... 600/102 |
| 2003/0052787 | A1 | 3/2003 | Zerhusen et al. |
| 2004/0152970 | A1 | 8/2004 | Hunter et al. |
| 2004/0152972 | A1 | 8/2004 | Hunter |
| 2004/0171924 | A1 | 9/2004 | Mire et al. |
| 2004/0199072 | A1 | 10/2004 | Sprouse et al. |
| 2004/0215071 | A1 | 10/2004 | Frank et al. |
| 2005/0245817 | A1 | 11/2005 | Clayton et al. |
| 2007/0038059 | A1 * | 2/2007 | Sheffer et al. ................. 600/407 |

* cited by examiner

*Primary Examiner* — Tung Vo
*Assistant Examiner* — Anner Holder
(74) *Attorney, Agent, or Firm* — McCracken & Frank LLP (57) ABSTRACT

A method and system includes multiple displays that can be separately controlled by users who are part of a surgical team. The first display will include information to assist a first user through the steps of a surgical procedure and the second display will assist a second user though the steps taken by the second user to perform the surgical procedure.

35 Claims, 11 Drawing Sheets

DISPLAY METHOD AND SYSTEM FOR SURGICAL PROCEDURES

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

This invention relates to display systems for use with a surgical navigation system. More particularly, this invention relates to a multiple display system for use with a surgical navigation system such that individual users can manipulate separate display screens.

2. Description of the Background of the Invention

Surgical navigation systems have become much more common within surgical suites. These systems assist a surgical team in the precise placement of tools and equipment. In addition, some surgical navigation systems also enable a surgical team to be more efficient by guiding the team stepwise through a pre-selected series of steps to complete a procedure. The display screens that guide the team can provide information to the team to enable the team to make appropriate choices given the current state of the procedure and the patient's anatomy. For instance, the system can prompt a team member to manipulate a limb of the patient during an orthopedic procedure to enable the system to locate relevant anatomical landmarks. The system can also provide alternate approaches based on the particular training and practice of the team. In many ways, the surgical navigation systems do much more than locate the anatomy of the patient relative to a particular surgical tool or implement. These systems also instruct and guide the surgical team through the procedure so that the team can be more efficient.

Even though surgical navigation systems enable a surgeon to be more precise, the use of surgical navigation systems often add to time needed to perform a surgical procedure. One reason is the use of a surgical navigation system changes the communication needed among the members of the surgical team. A further disadvantage to these surgical navigation systems is that the information is displayed on a single monitor or display within the surgical suite. The information displayed on the prior systems tends to be directed to the surgeon to assist the surgeon in precisely locating and manipulating the anatomy and/or the relevant instruments. In part, this is because it is difficult for multiple people to see what is shown on a single display. Also, if some of the display screens were directed towards other members of the surgical team, this could be cumbersome and reduce the overall efficiency of the team by requiring certain screens to be bypassed if the team member to which the screen is directed cannot see the display or is not close enough to respond to information requested by the display.

SUMMARY OF THE INVENTION

A method for facilitating a surgical procedure using a surgical navigation system, the method includes the steps of displaying a primary screen on a display device generated by the surgical navigation system, the primary screen including an image generated by the surgical navigation system, the primary screen being one of a plurality of primary screens that guide a first user through the surgical procedure, the primary screen being controllable by the first user; and displaying a secondary screen on a display device generated by the surgical navigation system, the secondary screen being related to the primary screen and the secondary screen being one of a plurality of secondary screens displaying information that guide a second user through the surgical procedure, the secondary screen being controllable by the second user independent from the control of the fist user. The method further includes the step of changing at least one of the primary screen and the secondary screen to another screen within the plurality of primary screens and plurality of secondary screens, the changing based on an interaction from at least one of the first user and the second user. A system to facilitate the performance of a surgical procedure includes a surgical navigation system, and one or more display devices that are driven by the surgical navigation system that can simultaneously display a first display screen and a separate second display screen associated with the procedure. The system also includes a first control device; and a second control device, wherein each display screen can be separately controlled by one of the first control device and the second control device to manipulate one of the first display screens and the second display screens, and wherein the first and second display screens display different but related information relative to the procedure. Other aspects and advantages of the present invention will become apparent upon consideration of the following detailed description.

DETAILED DESCRIPTION OF THE PREFERRED EMBODIMENTS

Figure 1:
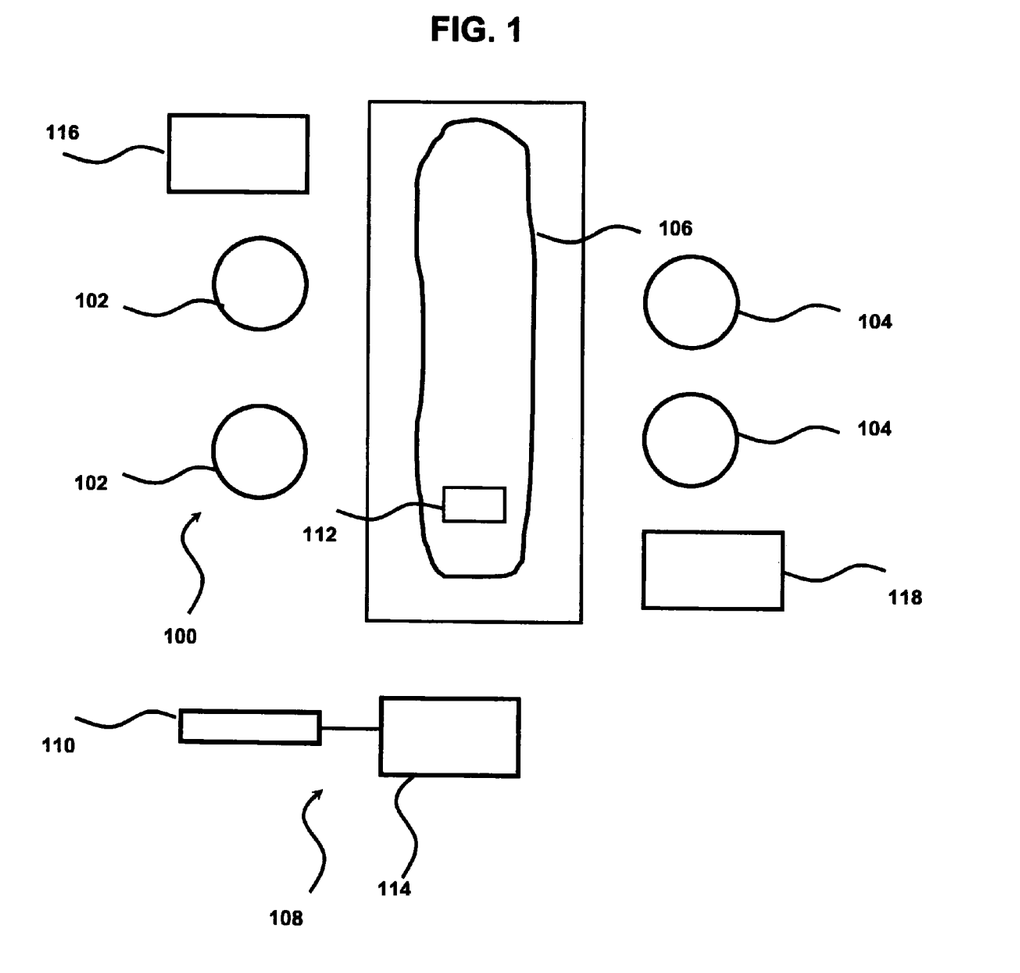
FIG. 1 a diagrammatic representation of a surgical team performing a procedure within a surgical suite using a surgical navigation system.

FIG. 1 shows in diagrammatic fashion a surgical team 100 that includes at least one surgeon 102 and one or more surgical assistants 104. The surgical team 100 is performing a procedure on a patient 106 using a surgical navigation system 108. The surgical navigation system 108 includes a camera 110 that can receive positional information from one or more tracking devices 112 associated with the patient 106. The surgical navigation system 108 also includes a computer 114 that has a cpu (not shown), memory (not shown) and a storage device, such as a hard drive (not shown). In addition, the surgical navigation system 108 includes a first display device 116 and a second display device 118 positioned so that at least one of the surgeons 102 can view and manipulate one of the first and second display devices 116 and 118 and at least one of the surgical assistants 104 can view and manipulate the other of the first and second display devices 116 and 118. The surgeons 102 and the assistants 104 will manipulate the display devices using pointing devices, including. a standard computer mouse (not shown) or a specialized surgical device (not shown) that is recognized by the camera 110 and computer 114. As opposed to a camera, any information receiving device could be used to receive input such as Electromagnetic waves, previously input data, X-ray imaging information, etc. with the system configured to process the information and display it on various display devices as described. It should be understood that the display devices 116 and 118 can be any type of device that is capable of generating an image including without limitation CRT devices, LCD devices, various flat screen devices, projection devices, user worn devices, virtual reality devices, heads up displays and the like.

Figure 2:
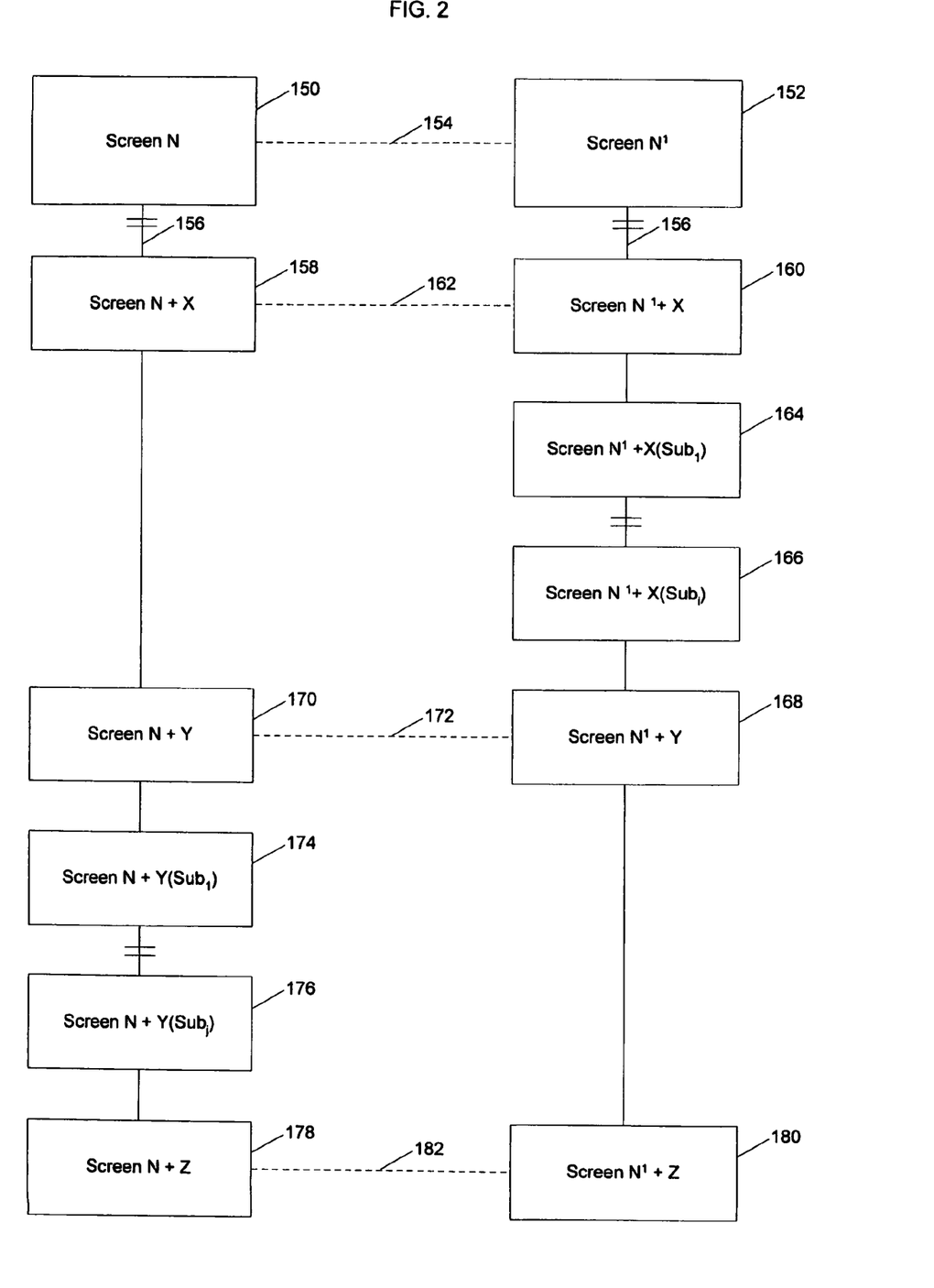
FIG. 2 is a flow diagram of one embodiment of the present invention.

FIG. 2 is a flow diagram of one embodiment of the system of the present invention. The surgical navigation system 108 will often display different screens on the first display device 116 and the second display device 118. A block 150 is a display screen N on the first display device 116 at the beginning of one aspect of a surgical procedure. The block 150 could be the initial screen for a particular procedure or could also be the first screen for a particular portion of the surgical procedure. At the same time, the surgical navigation system 108 will display at a block 152 a different display screen N' on the second display device. The display screen N of the block 150 and the display screen N' of the block 152 are related to each other as shown by dashed line 154. In this instance, the display screens N and N' of the blocks 150 and 152 display related information that is directed to the particular user of either the first display device 116 or the second display device 118. As an example, the display screen N of the block 150 could show a standard display screen typical of a surgical navigation system that provides information and/or instruction to the surgeon 102. The display screen N' of the block 152 might include a window showing what the surgeon 102 see on the display screen N of the block 150 and also provide the user of the display screen N' of the block 152 with information or instructions particularly tailored to the role of the user of the display screen N' of the block 152 within the surgical team. In certain embodiments, the user of both the first display device 116 and the second display device 118 might change to different people within the surgical team 100 during the procedure. This will depend on the flow of the particular surgical procedure and the number of people on a particular surgical team 100.

As noted above, the surgeons 102 can manually manipulate the display device 116 and the assistants can manually manipulate display device 118. In certain embodiments, the computer 114 can automatically advance one or both of the display devices 116 and/or 118 when the camera 110 detects that the surgeon 102 or the assistant 104 has picked up, moved or introduced a particular device that is within the view of the surgical navigation system 108 and can be located by the camera 110. This feature will minimize the manual interaction with the computer 114 by the members of the surgical team and at the same time advance the screens to keep pace with the course of the procedure. Such an application of this particular facet of the invention could be the use of RF (radiofrequency) technology. In this technology, an implanted chip in an instrument could signal the camera that the surgeon was going to perform a particular step and advance one or both screens/displays accordingly.

The user of the either display screen N of the block 150 or the display screen N' of the bock 152 may advance the particular display screen to further display screens within the procedure, as represented by broken lines 156. At some point further within the surgical procedure a block 158 display a screen N+X. At roughly the same time the user of the other display device advances to a block 160 that displays a screen N'+X. Again in this instance the screens N+X and N'+X are related in some fashion as shown by dashed line 162. At this point within the procedure the user of the screen N'+X has a series of follow on screens N'+X(sub1 to sub i) of blocks 164 and 166. The added screens represent additional steps that the user of the display screens N'+X(sub1 to sub i) must execute or informational screens with multiple screens of information needed by the user of screen N'+X(sub1 to sub i) where i is a number of sub steps that need to be accomplished by this particular user at this point in the procedure. After the user of the screen N'+X(sub i) has completed that tasks on that screen, the program advances to a display screen N'+Y at a block 168. At somewhat the same time, the user or the other display device will also have advanced directly from the screen N+X to a display screen N+Y of a block 170. Display screens N+Y and N'+Y are interrelated as indicated by dashed line 172.

At this point in the procedure, the user of display screen N+Y has a series of procedure step and or display screens N+Y(sub 1 to sub j) at blocks 174 and 176, where j is the number of sub screens, that must be accomplished before advancing to a display screen N+Z at a block 178. The advance to display screen N+Z is roughly contemporaneous with the other user advancing to a display screen N'+Z at a block 180. The screens of the block 178 and 180 are interrelated as indicated by dashed line 182. At this point in the procedure, the users will continue to advance through further screens, not shown, to complete the procedure. Also, it should be understood that the members of the surgical team can also go back to a previous screen or window if dictated by the course of the procedure. The particular screens and order of the display of the screens can be controlled in one embodiment by a database that is stored on the navigation computer 114. The content of this database can be customized by the members of the surgical team to reflect the teams particular approach to a certain procedure. The entire process can be customized to facilitate the efficient use of the surgical team's time and talents. The combination of the navigation system and the database can approximate an expert system in certain embodiments or the database can be a library of screens that can be displayed in a particular order based on choices made by the user as the program proceeds.

Figure 3:
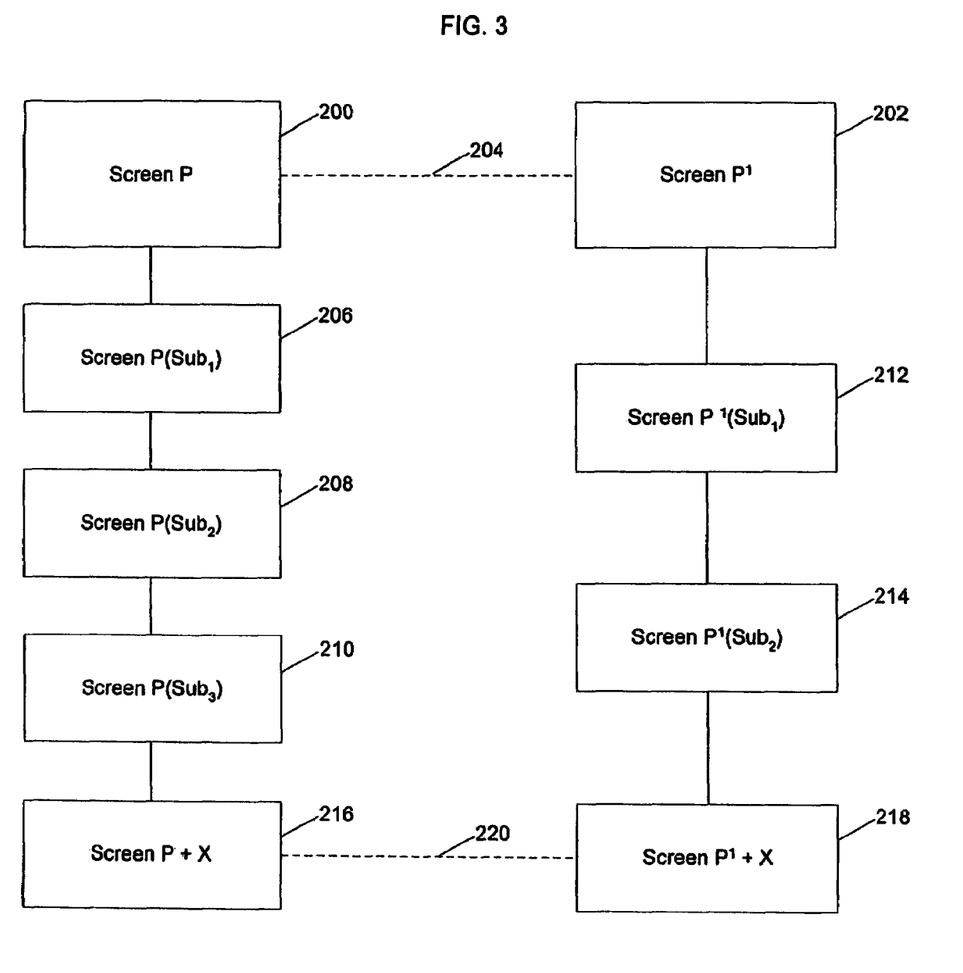
FIG. 3 is a flow diagram of another embodiment of the present invention.

FIG. 3 illustrates a further embodiment of the present invention. In this embodiment, at some point in the procedure, each of the users of the multiple display screens will have a multipart procedure to accomplish. However, the sub-screens of these two multipart procedures are not interrelated other than that they are performed at roughly the same time between two sets of display screens that are interrelated. The users begin at a display screen P in a block 200 and a display screen P' at a block 202. Display screens P and P' are interrelated as shown by dashed line 204. At this point, the user of display screen P has a three display screen sub-procedure to follow as shown by display screens P(sub 1 to sub 3) in blocks 206, 208, and 210. Also, the user of display screen P' has a two step procedure to accomplish at roughly the same time. Blocks 212 and 214 include display screens P'(sub 1) and P'(sub 2). The steps facilitated by display screens P'(sub 1) and P'(sub 2) are not directly related to the steps enabled by display screens P(sub 1 to 3) in that each series of display screens can proceed independent of the other and both must be performed before the respective users advance to interrelated display screens P+X and P'+X at blocks 216 and 218. Display screens P+X and P'+X are also interrelated as shown by dashed line 220.

Figure 4:
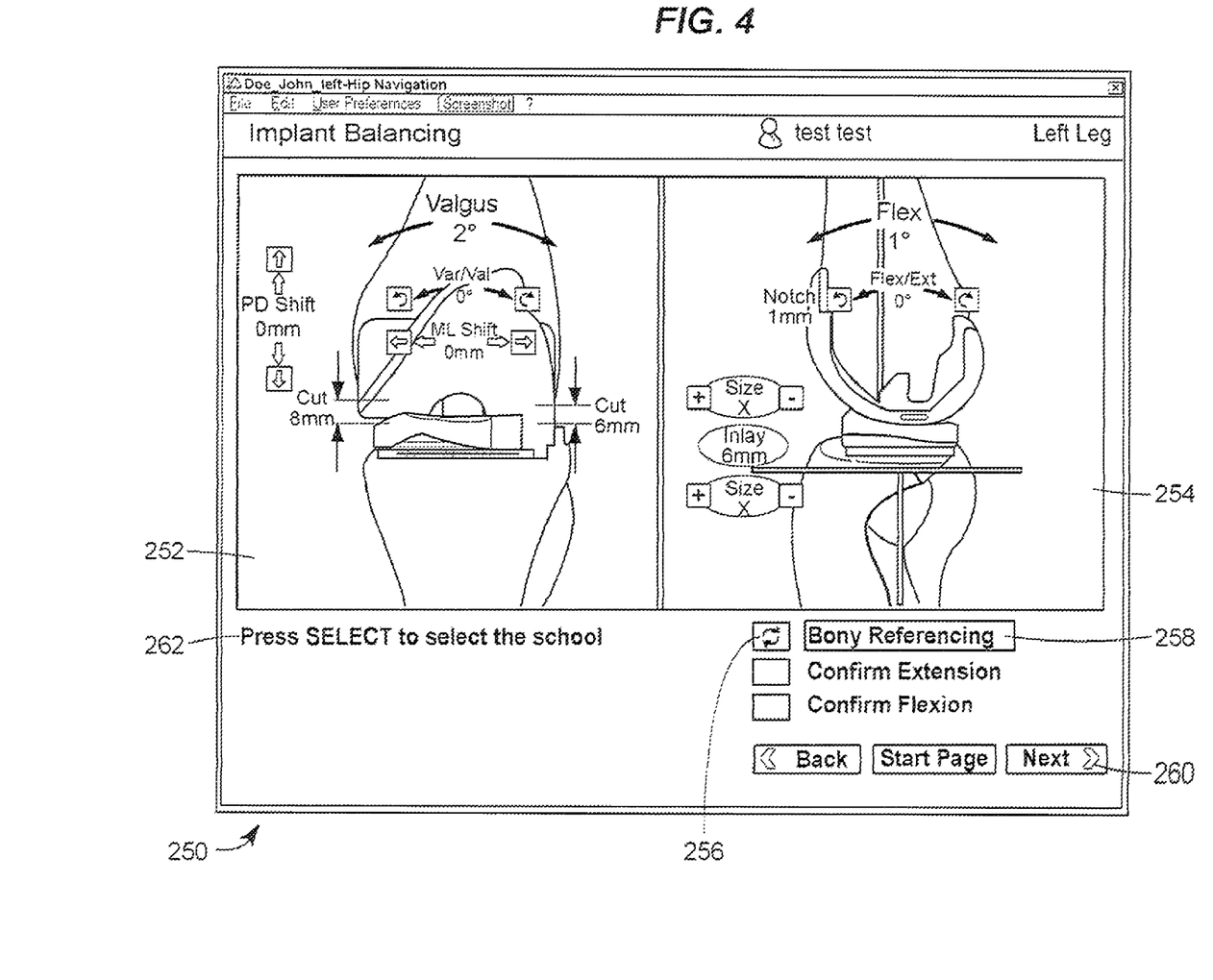
FIG. 4 is a representation of a further display screen for one user showing one step of a surgical procedure for that user according a further embodiment of the present invention.

FIG. 4 is a screen shot 250 from the display of the primary user of the system. Normally this will be one of the surgeons on the surgical team, but it also could be a technician that assists the surgeon. The display shown in screen shot 250 is typical of screens that are found in a surgical navigation system. The screen shot 250 includes a left window 252 and a right window 254. The screen shot 250 also includes a button 256 to choose a particular approach to the surgical procedure. The particular approach is shown in a text box 258 located next to the button 256. The text in the text box 258 will vary depending on the number of times the button 256 is pushed on the screen. Other buttons 260 and text 262 are also shown on the screen shot 250 as is typical of these types of display screens.

Figure 5:
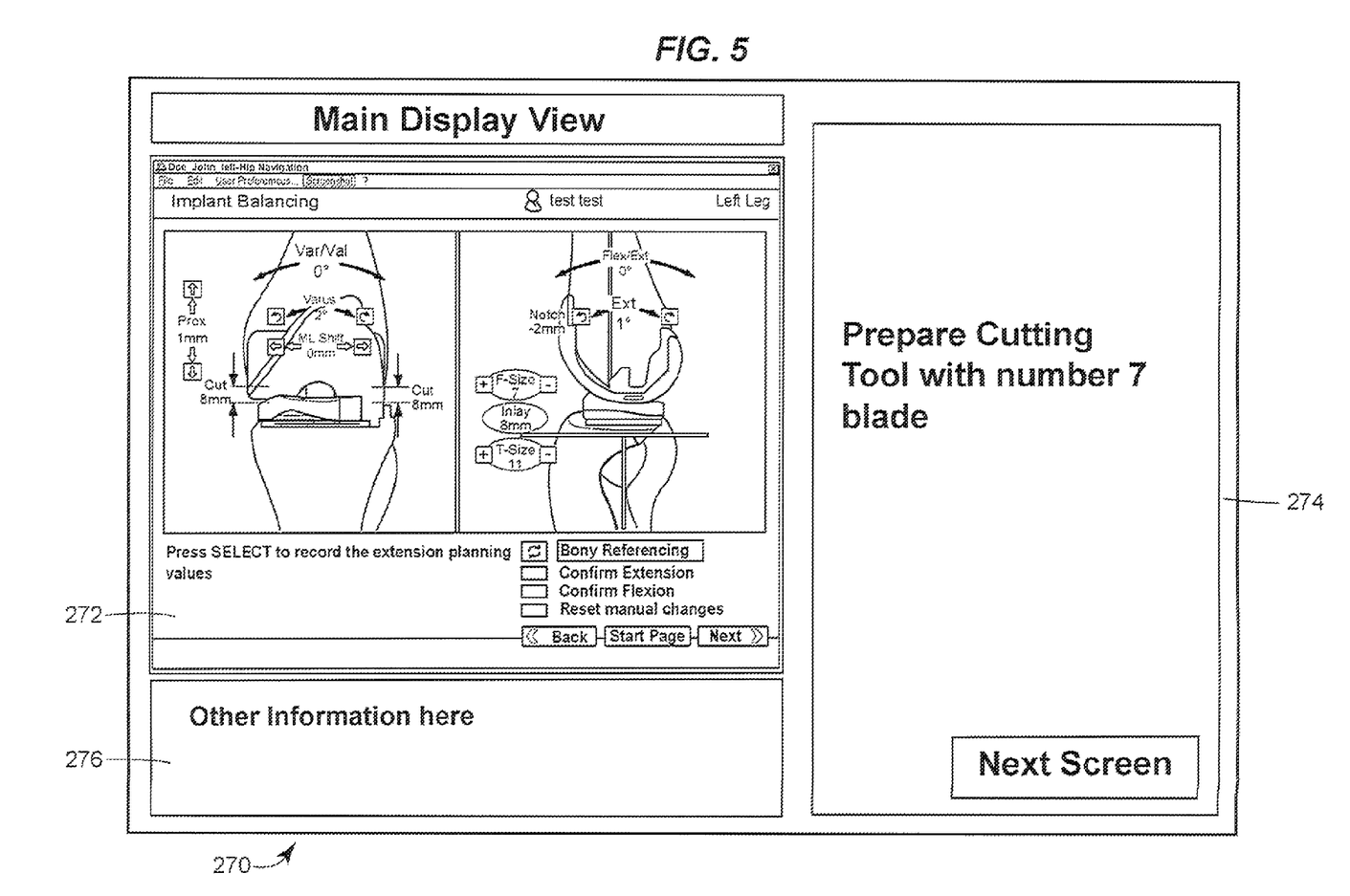
FIG. 5 is a representation of a display screen for a second user showing one step of a surgical procedure for the second user according an embodiment of the present invention.

FIG. 5 shows a screen shot 270 of one embodiment of a display screen that might appear on the display 118 used by the surgical assistant 104. The screen shot 270 includes a window 272 that is a miniaturized view of the display on the main display screen. The view in window 272 can be either a static representation of the view shown on the main display or the view in window 272 can dynamically update as the view on the display 116 is changed. The screen shot 270 also has a second window 274 that displays instructions that the surgical assistant is to perform at this particular stage in the procedure. In addition to text appearing in window 274, if appropriate, pictures, diagrams, views of pre-operative scans and the like can also appear in the window 274. The particular embodiment shown in screen shot 270 also has an optional third window 276. This window 276 can be used to display other information, such as a chosen set of monitored vital signs of the patient, tourniquet time, the time of the procedure, a timer for a particular portion of the procedure, and the like. In some embodiments there can be only two windows or there could be as many windows displayed as can conveniently fit on a display screen.

Figure 6:
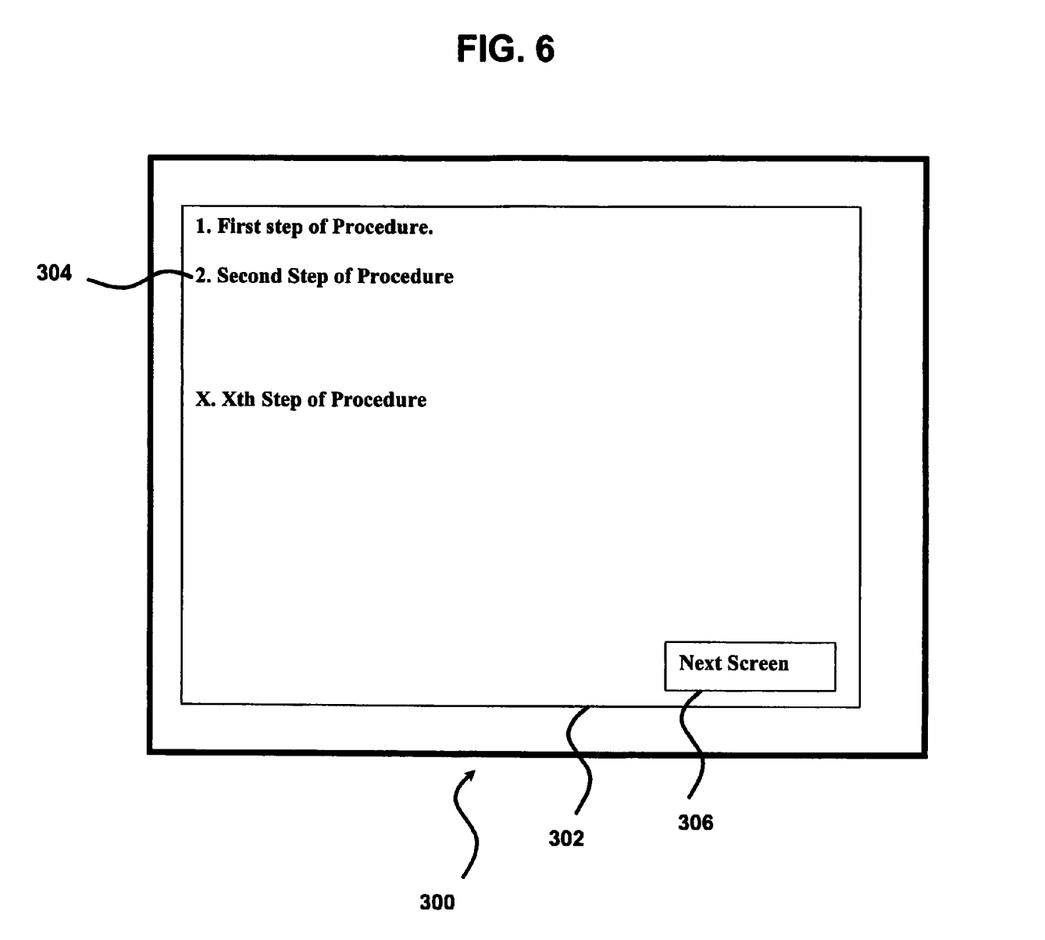
FIG. 6 is a representation of a display screen for a second user showing one step of a surgical procedure for the second user according a further embodiment of the present invention.

FIG. 6 shows a screen shot 300 of a further embodiment of a display screen that might appear on the display 118 used by the surgical assistant 104. The screen shot 300 has a single window 302 that displays a series of instructions 304. The window 302 may also include a button 306 and other text and information that are typically found on these types of display screens. In this instance the information displayed in window 302 is related to what is shown on the display screen 116 of the other user of the system.

Figure 7:
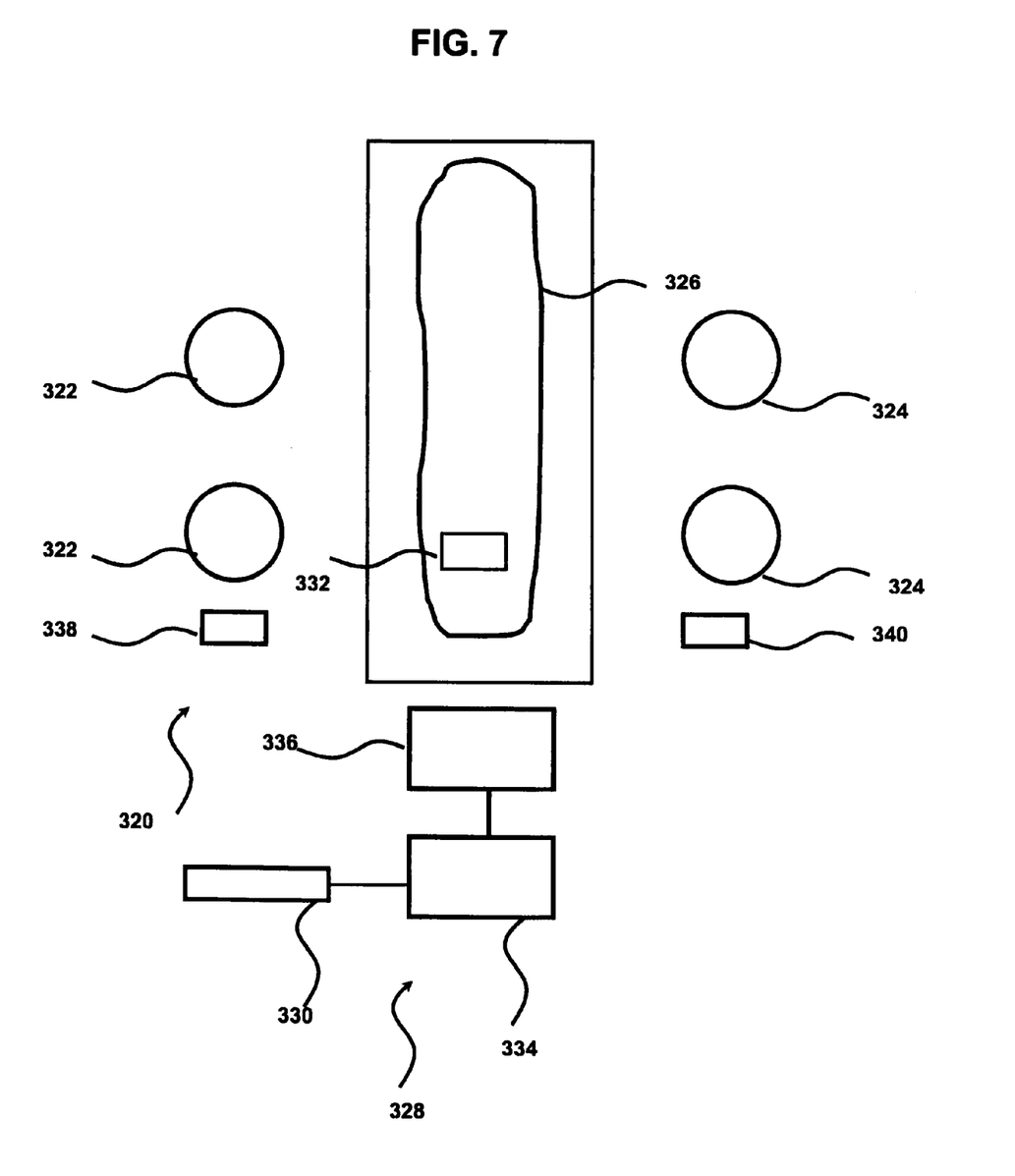
FIG. 7 is a diagrammatic representation of a further embodiment of the present invention.

FIG. 7 is a further embodiment 320 of the present invention. A patient 326 has been prepared for a particular procedure that will use a surgical navigation system 328. The surgical navigation systems 328 includes a camera 330 that can detect tracking devices 332 that can be associated with the patient 326 and/or a particular instrument that is used by either the surgeon 322 or the assistant 324. The surgical navigation system 328 also includes a computer 334 that includes an internal cpu (not shown) and storage device (not shown). In this embodiment, surgeons 322 and assistants 324 are all viewing a single display device 336 associated with the surgical navigation system 328 that can independently display two separately controllable windows. The surgeons 322 will use a control device 338, such as a computer mouse or specialized surgical control device, to control the surgeon's portion of the display on the display device 336. At the same time, the assistants 324 can use a similar control device 340 to control the display on the assistant's portion of the display on display device 336. Depending on the particular stage of the procedure, the relative size of the two portions can dynamically change so that the group that needs more display area on the display device 336 will have a larger portion of the display.

Figure 8:
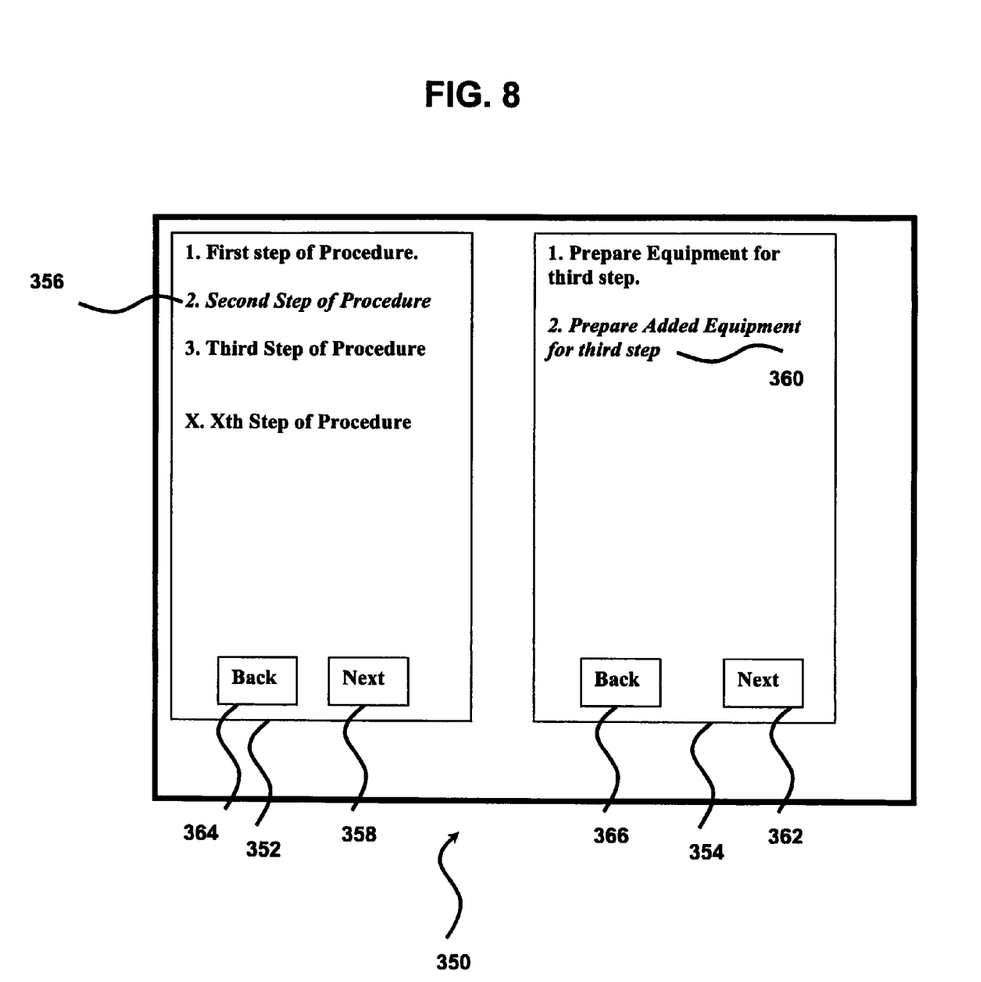
FIG. 8 is a further embodiment of a display of the present invention.

FIG. 8 is a schematic illustration of a display 350 that includes two separately controllable windows 352 and 354. Window 352 shows some textual instructions 356 that will be used by the surgeons 322. As shown, certain of the instructions can be highlighted to indicate the particular portion of the instructions that are currently active. Any form of highlighting can be used such as bolding the chosen instruction while at the same time graying out the remaining instructions, the use of different colors, fonts or type face or size, a highlight box, or other similar indications. In a similar manner, the window 354 also includes textual instructions 360. Also as shown, both windows include a box 358 and a box 362 to enable the particular team member to advance the screen or the instruction to the next screen or instruction. In a similar manner boxes 364 and 366 can take a user back an instruction or screen. Also, the system should enable a user to jump to a particular screen within the procedure at any time. There might be the need to skip certain steps or go to an alternate procedure depending on the circumstances encountered.

Figure 9:
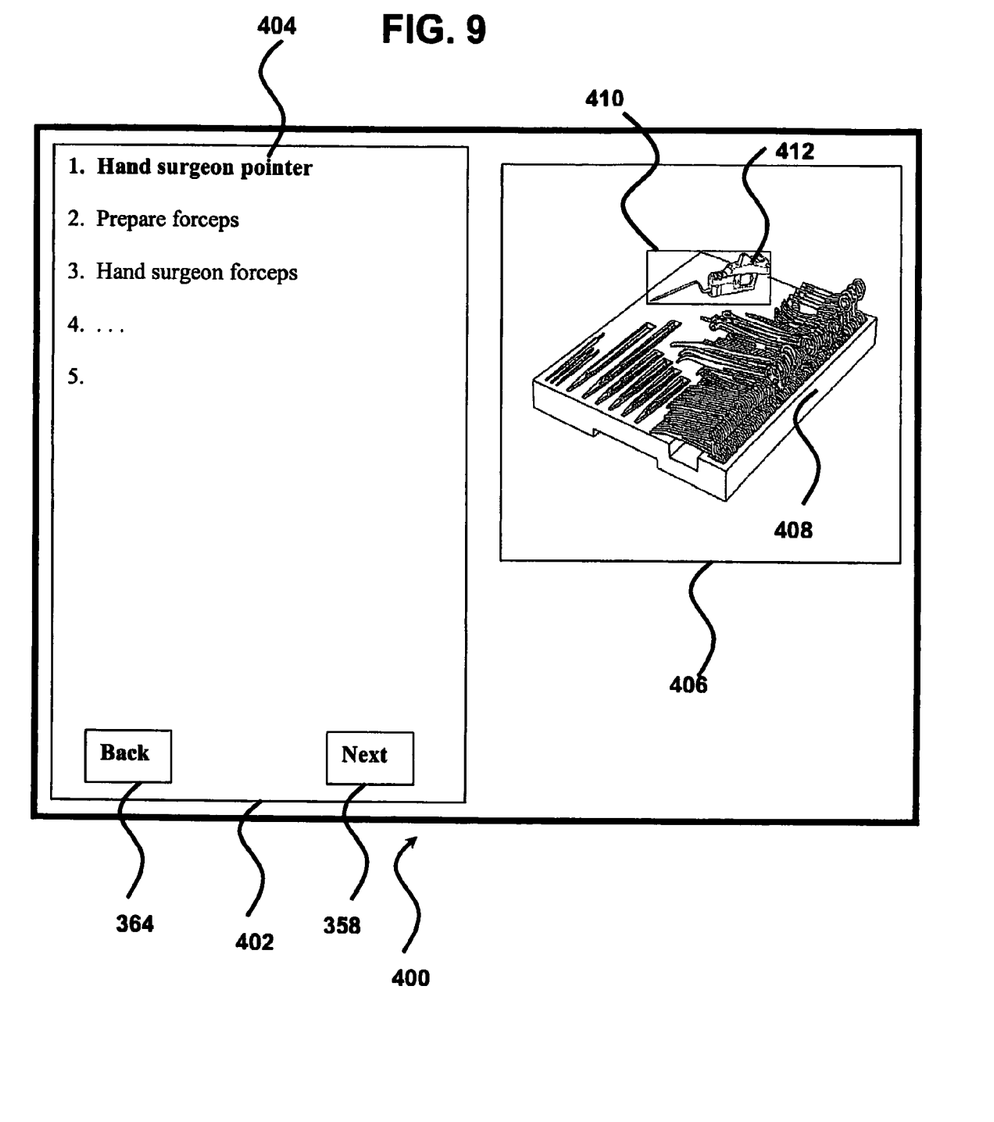
FIG. 9 is a still further embodiment of a display of the present invention.

In certain embodiments of the present invention, the surgical navigation system 108 can recognize the presence of a particular instrument or device that is brought within the filed of view of the surgical navigation system 108, and the surgical navigation system 108 can actually identify the type of instrument or device. These instruments are sometimes referred to as smart instruments and communicate directly to the surgical navigation system 108 using techniques that are will known. One example of these instruments is disclosed in United States Published Application 2001/0034340, the disclosure of which is hereby incorporated by reference. As shown in FIG. 9, the surgical navigation system 108 can include layouts of trays of instruments that will be used in the particular procedure. Display 400 includes a window 402 with step by step instructions 404. Window 400 also includes a second window 406 that includes a representation 408 of the tray of instruments to be used, at least in part, during that portion of the procedure. In one embodiment, the representation 408 will highlight 410 the particular instrument to be handed to the surgeon next, in this instance a trackable pointer 412. This highlight can be in any number of ways well know to those in the art, including having the representation of the particular instrument colored differently, surrounded by a shape, such as a circle, appear to float above the other instruments, etc. Also, the system could cause a light or other indicator on the particular instrument to flash or change color so that the assistant can more easily identify and choose the correct instrument.

Figure 10:
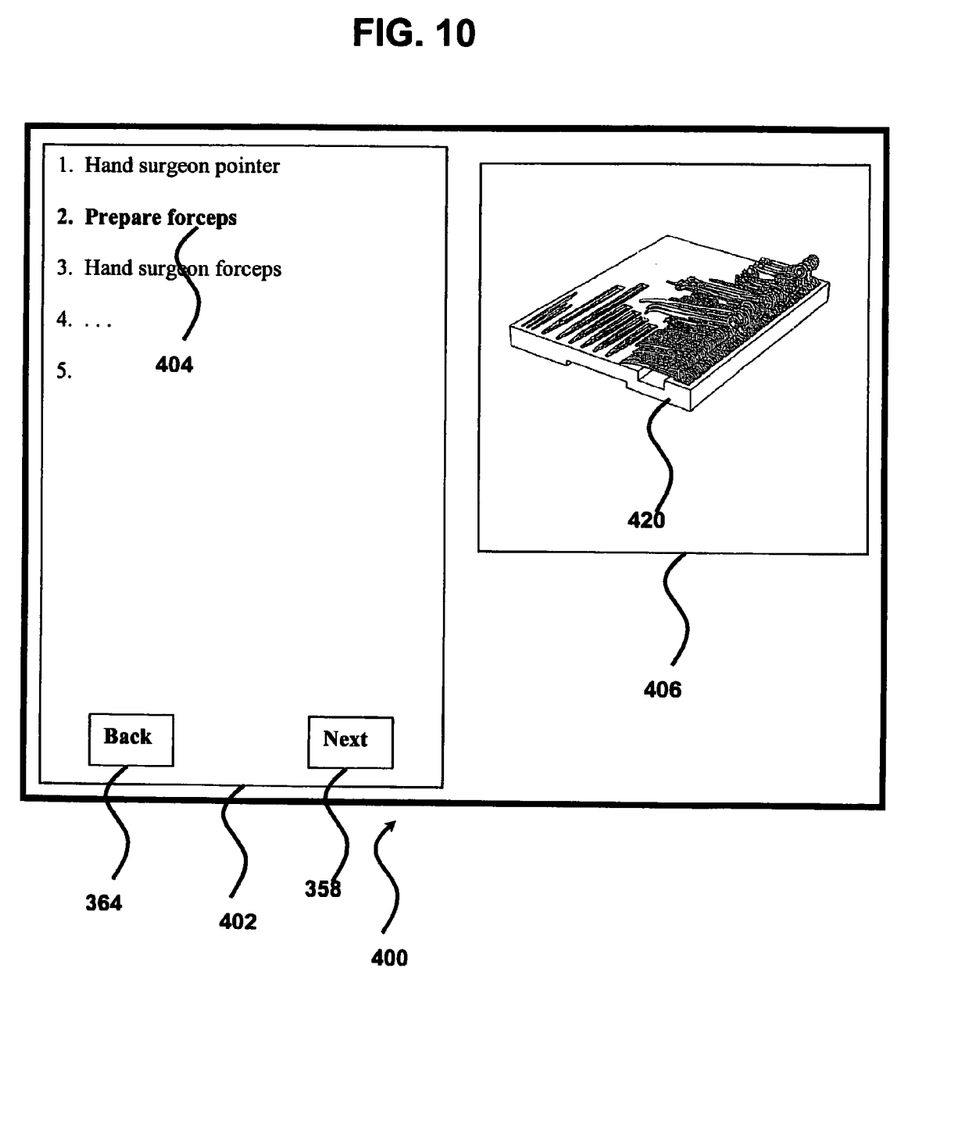
FIG. 10 is a view of an updated display of FIG. 9.
Figure 11:
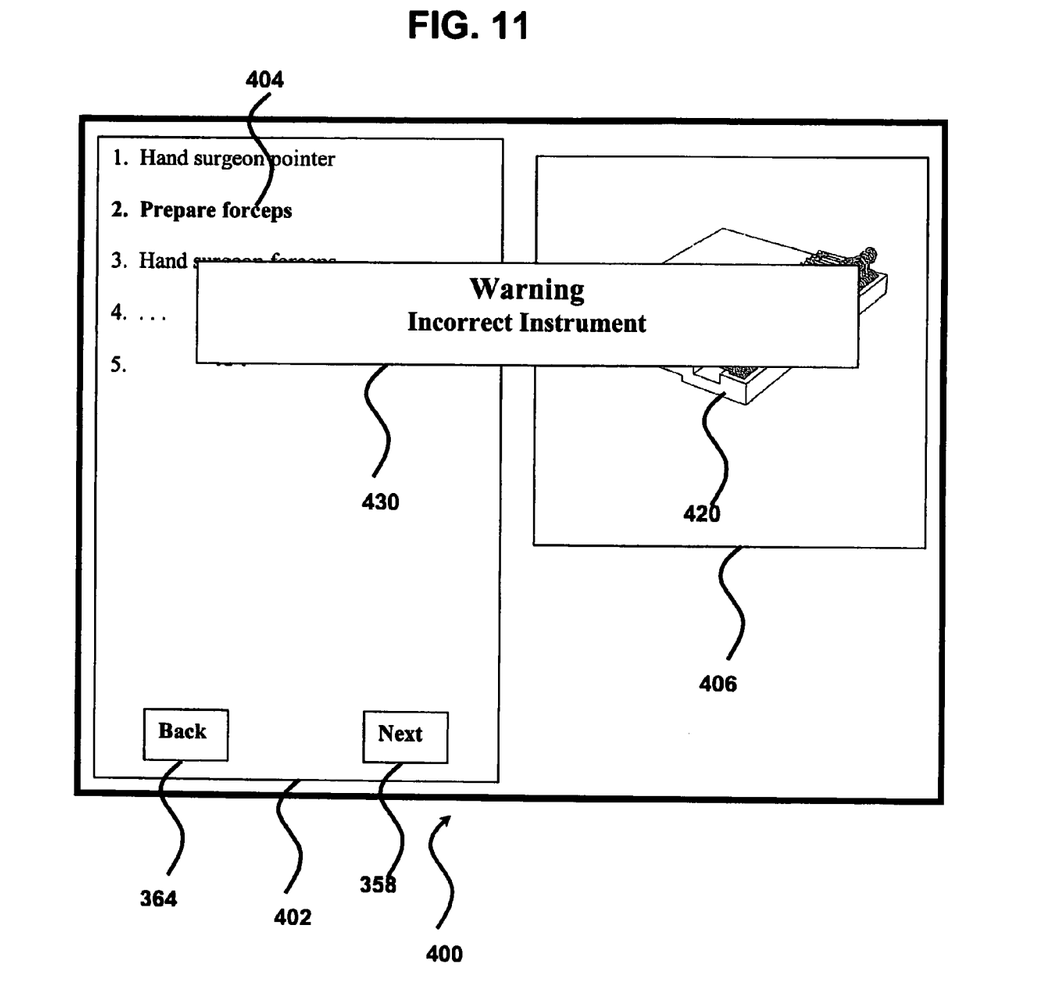
FIG. 11 is a view of FIG. 9 that includes an added embodiment of the present invention.

In addition, because the instruments can be recognized by the surgical navigation system 108, the representation 408 can be updated as shown in FIG. 10 to a representation 420 that shows the instrument removed from the tray. Most other aspects of the window 400 are unchanged, except for updated information 422 that has moved on to the next step. Also, if the tray is within the field of view of the surgical navigation system 108, the surgical navigation system 108 can also determine if an incorrect instrument has been picked up. In this case, the instrument itself could warn the user by flashing status lights, vibrating or use of some other warning method. In addition, as shown in FIG. 11, a warning 430 could be splashed on top of the window 400 in a contrasting color to warn the user.

INDUSTRIAL APPLICABILITY

The present invention is useful in facilitating and assisting in the performance of surgical and other precision procedures that are performed by a group using navigation technology.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A method for facilitating a surgical procedure using a surgical navigation system, the method comprising the steps of:
    displaying a primary screen on a display device generated by the surgical navigation system, the primary screen including an image generated by the surgical navigation system, the primary screen being one of a plurality of primary screens that guide a first user through the surgical procedure, the primary screen being controllable by the first user;
    displaying a secondary screen on a display device generated by the surgical navigation system, the secondary screen being related to the primary screen and the secondary screen being one of a plurality of secondary screens displaying information that guide a second user through the surgical procedure, the secondary screen being controllable by the second user independent from the control of the first user;
    changing at least one of the primary screen and the secondary screen to another screen within the plurality of primary screens and plurality of secondary screens, the changing based on an interaction from at least one of the first user and the second user; and
    providing a warning if an incorrect instrument is picked up.

2. The method of claim 1 wherein the primary screen and the secondary screen are on the same display device.

3. The method of claim 1 wherein the primary screen and the secondary screen are on separate display devices.

4. The method of claim 1 wherein the changing is based on movement of a device within the view of the surgical navigation system.

5. The method of claim 1 wherein the changing is also based on an interaction of one of the users with the surgical navigation system.

6. The method of claim 1 wherein the changing is also based on a database within the surgical navigation system.

7. The method of claim 1 wherein the secondary screen will also display screens not related to the primary screen between two screens that are related to the primary screen.

8. The method of claim 1 wherein the primary screen will also display screens that do not have a relation to a secondary screen in between primary screens that do have a relation to respective secondary screens.

9. The method of claim 1 wherein the secondary screen displays information shown on the related primary screen in addition to information specific to that particular secondary screen.

10. The method of claim 9 wherein the secondary screen also displays additional information that is useful to the second user.

11. The method of claim 10 wherein the additional information includes vital sign information that is updated in real time.

12. The method of claim 1 wherein the secondary screen displays information relating to the appropriate stage of the surgical procedure.

13. The method of claim 12 wherein the secondary screen also displays additional information that is useful to the second user.

14. The method of claim 13 wherein one of the display screens also includes information that is currently being shown on the other display screen.

15. The method of claim 1 wherein either user can jump to a particular screen at any time.

16. The method of claim 1 wherein one of the screens includes a representation of a tray of surgical instruments.

17. The method of claim 16 wherein the screen highlights the representation to identify the next surgical instrument to be used.

18. The method of claim 1 that includes indicating a next instrument to be used.

19. The method of claim 18 wherein the indicating is provided by the instrument itself.

20. The method of claim 1 wherein the warning is provided by the tool itself.

21. The method of claim 1 wherein the warning is displayed on the display device.

22. A system to facilitate the performance of a surgical procedure comprising:
    a surgical navigation system;
    one or more display devices that are driven by the surgical navigation system that can simultaneously display a first display screen and a separate second display screen associated with the procedure;
    a first control device; and
    a second control device,
    wherein each display screen can be separately controlled by one of the first control device and the second control device to manipulate one of the first display screens and the second display screens, and wherein the first and second display screens display different but related information relative to the procedure, and
    wherein the system provides a warning if an incorrect instrument is picked up.

23. The system of claim 22 wherein the first and the second display screens are displayed on a single display device.

24. The system of claim 22 wherein the first and the second display screens are displayed on separate display devices.

25. The system of claim 22 wherein the display screen can be advanced by movement of an instrument within the view of the surgical navigation system.

26. The system of claim 22 that also includes a database that can interact with the user to change the display screen.

27. The system of claim 22, wherein one of the display screens also displays some of the information shown at the same time on the other display screen.

28. The system of claim 22 wherein one of the display screens includes a representation of a tray of surgical instruments.

29. The system of claim 28 wherein the representation highlights the next surgical instrument to be used.

30. The system of claim 22 wherein one or both of the display screens displays information not related to the navigation system but important to one or more of the users.

31. The system of claim 22 wherein the system indicates a next instrument to be used.

32. The system of claim 31 wherein the next instrument itself provides the indication.

33. The system of claim 22 wherein the warning is provided by the instrument itself.

34. The system of claim 22 wherein the warning is provided on the display device.

35. The method of claim 13 wherein the additional information includes vital sign information that is updated in real time.

* * * * *